United States Patent
Ma et al.

(10) Patent No.: US 9,938,215 B2
(45) Date of Patent: Apr. 10, 2018

(54) PROCESS OF MAKING BIODERIVED PROPYLENE GLYCOL

(71) Applicant: ARCHER DANIELS MIDLAND COMPANY, Decatur, IL (US)

(72) Inventors: Chi-Cheng Ma, Forsyth, IL (US); Todd Werpy, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/304,666

(22) PCT Filed: Apr. 9, 2015

(86) PCT No.: PCT/US2015/025092
§ 371 (c)(1),
(2) Date: Oct. 17, 2016

(87) PCT Pub. No.: WO2015/164088
PCT Pub. Date: Oct. 29, 2015

(65) Prior Publication Data
US 2017/0036975 A1   Feb. 9, 2017

Related U.S. Application Data

(60) Provisional application No. 61/982,608, filed on Apr. 22, 2014.

(51) Int. Cl.
*C07C 29/60* (2006.01)
*C07C 29/151* (2006.01)

(52) U.S. Cl.
CPC .......... *C07C 29/60* (2013.01); *C07C 29/1512* (2013.01)

(58) Field of Classification Search
CPC ........................... C07C 29/1512; C07C 29/60
See application file for complete search history.

(56) References Cited

U.S. PATENT DOCUMENTS 6,841,085 B2 *   1/2005   Werpy .................... C07C 29/00
                                                                        252/1

* cited by examiner

*Primary Examiner* — Pancham Bakshi
*Assistant Examiner* — Mark R Luderer
(74) *Attorney, Agent, or Firm* — William B. Miller

(57) ABSTRACT

An improved process for making bioderived propylene glycol from a feed composition including at least one of lactic acid, glycerol, a five carbon sugar, a five carbon sugar alcohol, a six carbon sugar and a six carbon sugar alcohol, wherein production of four carbon and higher diols is reduced by adding base after the initiation of the reaction. In preferred embodiments, the process pH and other process conditions are initially established at targeted values for obtaining the highest conversion for a given catalyst consistent with the production of substantially no pentanediol byproducts in the product mixture, and base is added thereafter to control the process pH proximate to the initially targeted value.

9 Claims, No Drawings

PROCESS OF MAKING BIODERIVED PROPYLENE GLYCOL

BACKGROUND

This invention relates generally to processes for making a bioderived propylene glycol (1,2-propanediol). More particularly, the present invention relates to methods for making a bioderived propylene glycol through the reaction of a biobased feedstock—conventionally, glycerol, five and six carbon sugars and/or sugar alcohols and/or lactic acid—with hydrogen to provide a polyol product mixture including propylene glycol, wherein the polyol product mixture is further processed to yield a commercially acceptable biobased equivalent to the petroleum-based or -derived commodity propylene glycol product used today in so many different applications.

The present invention is thus generally concerned with the development of renewably sourced products which are able to serve as commercially acceptable replacements for materials, and especially commodities such as propylene glycol and ethylene glycol, which are presently largely made downstream of conventional fossil fuel operations. Such biobased, renewably sourced materials can be differentiated from their petroleum-derived counterparts, for example, by their carbon isotope ratios using ASTM International Radioisotope Standard Method D 6866, the disclosure of which is incorporated by reference in its entirety. Method D 6866 is based upon the fact that isotopic ratios of the isotopes of carbon within any given material, such as the 13C/12C carbon isotopic ratio or the 14C/12C carbon isotopic ratio, can be determined using certain established analytical methods, such as isotope ratio mass spectrometry, with a high degree of precision.

ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D 6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products. As used herein, "biologically derived", "bioderived", and "biobased" may be used interchangeably to refer to materials whose carbon content is shown by ASTM D 6866, in whole or in significant part (for example, at least about 20 percent or more), to be derived from or based upon biological products or renewable agricultural materials (including but not limited to plant, animal and marine materials) or forestry materials.

Propylene glycol and ethylene glycol have, as mentioned previously, conventionally been produced from petrochemical sources. Commercial production of petroleum-based or -derived propylene glycol involves the hydration of propylene oxide, made predominantly by the oxidation of propylene. The commercial production of ethylene glycol similarly involves the hydration of ethylene oxide, made by the oxidation of ethylene. Propylene and ethylene in turn are industrial by-products of gasoline manufacture, for example, as by-products of fluid cracking of gas oils or steam cracking of hydrocarbons.

The world's supply of petroleum is, however, being depleted at an increasing rate. As the available supply of petroleum decreases or as the costs of acquiring and processing the petroleum increase, the manufacture of various chemical products derived therefrom (such as propylene glycol and ethylene glycol) will be made more difficult. Accordingly, in recent years much research has taken place to develop suitable biobased propylene glycol and ethylene glycol products, which can be interchangeable with propylene glycol and ethylene glycol products deriving from petroleum refining and processing methods but which are made from renewable versus nonrenewable materials.

As a result of these efforts, processes have been developed by several parties involving the hydrogenolysis of especially five and six carbon sugars and/or sugar alcohols, whereby the higher carbohydrates are broken into fragments of lower molecular weight to form compounds which belong to the glycol or polyol family. Sugars containing five carbon chains, such as ribose, arabinose, xylose and lyxose, lactic acid and five carbon chain sugar alcohols such as xylitol and arabinitol, are among the materials contemplated in U.S. Pat. No. 7,038,094 to Werpy et al., for example, while six carbon sugars such as glucose, galactose, maltose, lactose, sucrose, allose, altrose, mannose, gulose, idose and talose and six carbon chain sugar alcohols such as sorbitol are addressed by U.S. Pat. No. 6,841,085 to Werpy et al. (hereafter, "Werpy '085"). Some of these carbohydrate-based feedstocks are commercially available as pure or purified materials. These materials may also be obtained as side-products or even waste products from other processes, such as corn processing. The sugar alcohols may also be intermediate products produced in the initial stage of hydrogenating a sugar.

For other known examples of such processes, U.S. Pat. No. 5,206,927 describes a homogeneous process for hydrocracking carbohydrates in the presence of a soluble transition metal catalyst to produce lower polyhydric alcohols. A carbohydrate is contacted with hydrogen in the presence of a soluble transition metal catalyst and a strong base at a temperature of from about 25° C. to about 200° C. and a pressure of from about 15 to about 3000 psi. However, as is evident from Tables II and III in the disclosure of U.S. Pat. No. 5,206,927, about 2-7% of other polyol compounds are produced in the hydrocracking process. U.S. Pat. No. 4,476,331 describes a two stage method of hydrocracking carbohydrates using a modified ruthenium catalyst. European Patent Applications EP-A-0523 014 and EP-A-0 415 202 describe a process for preparing lower polyhydric alcohols by catalytic hydrocracking of aqueous sucrose solutions at elevated temperature and pressure using a catalyst whose active material comprises the metals cobalt, copper and manganese. Still other examples of such carbohydrate-based processes may be found without difficulty by those skilled in the art.

Other efforts have been based on the use of another readily accessible biobased feedstock, namely, glycerol. Glycerol is currently produced as a byproduct in making biodiesel from vegetable and plant oils, through the transesterification reaction of lower alkanols with higher fatty acid triglycerides to yield lower alkyl esters of higher fatty acids and a substantial glycerol byproduct. Glycerol is also available as a by-product of the hydrolysis reaction of water with higher fatty acid triglycerides to yield soap and glycerol. The higher fatty acid triglycerides may derive from animal or vegetable (plant) sources, or from a combination of animal and vegetable sources as well known, and a variety of processes have been described or are known.

A biobased glycerol is also available as a product of the hydrogenolysis of sorbitol, as described in an exemplary process in U.S. Pat. No. 4,366,332, issued Dec. 28, 1982.

U.S. Pat. Nos. 5,276,181 and 5,214,219 describe a process of hydrogenolysis of glycerol using copper and zinc catalyst in addition to sulfided ruthenium catalyst at a pressure over 2100 psi and temperature between 240-270° C.

U.S. Pat. No. 5,616,817 describes a process of preparing 1,2-propanediol (more commonly, propylene glycol) by catalytic hydrogenolysis of glycerol at elevated temperature and pressure using a catalyst comprising the metals cobalt, copper, manganese and molybdenum.

German Patent DE 541362 describes the hydrogenolysis of glycerol with a nickel catalyst.

Persoa & Tundo (Ind. Eng. Chem. Res. 2005, 8535-8537) describe a process for converting glycerol to 1,2-propanediol by heating under low hydrogen pressure in presence of Raney nickel and a liquid phosphonium salt. Selectivities toward 1,2-propanediol as high as 93% were reported, but required using a pure glycerol and long reaction times (20 hrs).

Crabtree et al. (Hydrocarbon processing Feb 2006 pp 87-92) describe a phosphine/precious metal salt catalyst that permit a homogenous catalyst system for converting glycerol into 1,2-propanediol. However, low selectivity (20-30%) was reported.

Other reports indicate use of Raney copper (Montassier et al. Bull. Soc. Chim. Fr. 2 1989 148; Stud. Surf. Sci. Catal. 41 1988 165), copper on carbon (Montassier et al. J. Appl. Catal. A 121 1995 231)), copper-platinum and copper ruthenium (Montassier et al. J. Mol. Catal. 70 1991 65). U.S. Pat. No. 7,790,937 to Henkelmann et al. similarly describes converting a glycerol-containing stream, especially a glycerol-containing stream obtained from biodiesel production, to propylene glycol by reaction with hydrogen in the presence of a heterogeneous catalyst containing copper. Raney copper and copper-containing metal alloys in the form of a Raney catalyst are mentioned as preferred.

Still other homogenous catalyst systems such as tungsten and Group VIII metal-containing catalyst compositions have also been tried (U.S. Pat. No. 4,642,394). Miyazawa et al. (J. Catal. 240 2006 213-221) & Kusunoki et al (Catal. Comm. 6 2005 645-649) describe a Ru/C and ion exchange resin for conversion of glycerol in aqueous solution.

The previously-cited Werpy '085 reference contemplates conversion of a composition including glycerol to bioderived propylene glycol by reaction with hydrogen in the presence of a Re-containing multimetallic catalyst.

Numerous other examples of like processes may be found without difficulty by those skilled in the art.

One of the recognized problems in producing a biobased propylene glycol or ethylene glycol by any of these methods, however, is that other diol compounds are formed (e.g., four carbon and higher diols) to varying degrees in all of these processes. The boiling points of many of these materials are very close to one another, so that the separation of high purity bioderived propylene glycol from these other polyhydric alcohols is exceedingly difficult by conventional distillation methods—such that substantial amounts of the desired propylene glycol product are inevitably co-distilled with the higher diols in order to remove these to the extent needed for many commercial applications.

Several reports in the literature describe efforts for azeotropically separating the other polyhydric alcohols from propylene glycol. For instance, U.S. Pat. No. 4,935,102 describes a method for using an azeotrope forming agent such as propylene glycol isobutyl ether, tetrahydrofurfuryl alcohol, N,N-dimethylacetamide, ethylene glycol diethyl ether, diethylene glycol diethyl ether, 2-methoxyethyl ether, ethylene glycol n-butyl ether, diacetone alcohol and ethyl n-butyl ketone. In U.S. Pat. No. 5,423,955, the azeotrope forming agent consists of a material selected from the group consisting of toluene, ethyl benzene, o-xylene, p-xylene, cumene, m-diisopropyl benzene, m-diethyl benzene, mesitylene, p-cymene, hexane, cyclohexane, methyl cyclohexane, heptane, 3-methyl pentane, octane, decane, 2,3,4-trimethyl pentane, dipentene, decalin, dicyclopentadiene, alpha-phellandrene, limonene, hemimellitene, myrcene, terpinolene, p-mentha-1,5-diene, beta-pinene, 3-carene, 1-heptene, cyclopentane, pentane, o-diethyl benzene, 2,2-dimethyl butane and 2-methyl butane.

Alternative approaches to purifying the product mixture have been proposed in commonly-assigned United States Patent Application Publication US 2008/0275277A1 to Kalagias, published Nov. 6, 2008, wherein the addition of a polar solvent and extractive distillation are presented as an alternative to the use of an azeotropic agent, and in commonly-assigned United States Patent Application Publication US2009/0120878A1 to Hilaly et al., published May 14, 2009, wherein simulated moving bed chromatography is offered as a means to achieve a purified, commercial grade biobased propylene glycol.

Nevertheless, the separation of a number of byproducts from the desired bioderived propylene glycol remains difficult and costly. The presence of four carbon and higher diols can in particular mean substantial losses of co-distilled propylene glycol product where conventional distillation methods are desired to be used for product purification, so that a process which enables a lesser amount of byproduct higher diols would be welcomed.

SUMMARY OF THE INVENTION

In one aspect, the present invention concerns such a process, whereby in a process for making bioderived propylene glycol by reacting a feed composition including at least one of lactic acid, glycerol, a five carbon sugar, a five carbon sugar alcohol, a six carbon sugar and a six carbon sugar alcohol with hydrogen in the presence of a suitable catalyst under conditions effective to carry out the conversion, production of four carbon and higher diols is reduced by adding base after the initiation of the reaction. In a continuous process, a base is added at one or more locations downstream of where the hydrogen and feed composition are initially combined under reaction conditions in the presence of the catalyst, while in a batchwise or semi-batch mode, a base is added at least once after the start of a batch.

In preferred embodiments, the process pH and other process conditions are initially established at targeted values for realizing or substantially realizing the highest conversion for a given catalyst consistent with the production of substantially no pentanediol byproducts in the product mixture, and base is added thereafter to control the process pH proximate to the initially targeted value after the initiation of the reaction, as needed to achieve a desired overall conversion rate while substantially avoiding the base-catalyzed formation of pentanediol byproducts in the process.

As background to our process as thus summarized, while the addition of base to a feed comprised of glycerol in aqueous solution has been found to enhance the reactivity of Pt and Ru catalysts to significantly varying degrees in converting glycerol to propylene glycol, see Maris et al., "Hydrogenolysis of glycerol over carbon-supported Ru and Pt catalysts", *Journal of Catalysis*, vol. 249, pp. 328-337 (2007), is prescribed in U.S. Pat. No. 4,338,472 to Sirkar for preventing the leaching of porous nickel from a supported nickel catalyst and in fact has been described as "necessary" for high conversion rates of glycerol to 1,2-propanediol (propylene glycol) in U.S. Pat. No. 5,276,181 to Casale et al., yet U.S. Pat. No. 5,616,817 to Schuster et al. asserts the addition of "substantial" base (e.g., 10 to 45% by weight of sodium hydroxide in the Casale et al. process) accomplishes "virtually quantitative conversion . . . at the expense of selectivity", col. 1, lines 35-37.

At the same time, in U.S. Pat. Nos. 7,928,148 and 8,153,847 (both to Bloom) we discovered unexpectedly that some of the loss in selectivity noted in Schuster et al. (albeit using a different catalyst) in the hydrogenolysis of glycerol to propylene glycol was attributable to the formation of higher diols, e.g., butanediols (1,2-butanediol, 1,3-butanediol, 1,4-butanediol, 2,3-butanediol and 2,4-butanediol) and at least one pentanediol (2,4-pentanediol). The Bloom patents contend that the formation of these butanediols can be minimized by various means, including adding a base at a level sufficient to ensure the selectivity of the catalyst toward propylene glycol is not diminished as organic acids such as lactic acid are formed which will cause the pH to drop in the reactor and will bring about a "concomitant reduction in the selectivity of the catalyst", see col. 9, lines 2-4 of U.S. Pat. No. 7,928,148 for example.

Consequently, while Maris et al., Sirkar and the Bloom patents collectively indicate that addition of a base is beneficial in the hydrogenolysis of glycerol for improving the activity of an hydrogenolysis catalyst, for guarding against acid-leaching of metals from the catalyst and for reducing the formation of butanediols, and while Schuster et al. suggests that addition of "substantial" base will in fact reduce the selectivity of hydrogenolysis catalysts to the desired, bioderived propylene glycol product, nevertheless Schuster et al. does not mention four-carbon and higher diols as being formed instead of propylene glycol and neither Bloom patent references Schuster et al. or expressly suggests that formation of four-carbon and higher diols will be increased by adding base beyond a certain extent if all of the other aspects said by the Bloom patents to influence butanediol formation—including operating at certain liquid hourly space velocities and certain temperatures and at certain combinations of these—are maintained. Moreover, neither of the Bloom patents nor Schuster et al. appreciates that even where "substantial" base is not added—in other words, where the selectivity to the desired propylene glycol product is not significantly reduced—nevertheless the difference in the amounts of four carbon and higher diols that are formed at different amounts of added base can be consequential, in terms of the viability of product purification by conventional distillation methods. As mentioned previously, the presence of four carbon and higher diols can mean substantial losses of co-distilled propylene glycol product where conventional distillation methods are desired to be used for product purification.

By adding base after the beginning of the hydrogenolysis reaction, at one or preferably at a plurality of locations downstream along the length of a continuous reactor or at least once or preferably on a plurality of occasions after the initiation of a batch in a batchwise or semi-batch process, a process of the present invention enables sufficient alkalinity to be realized downstream in a continuous reactor or later in a batch to promote the activity of a catalyst for the hydrogenolysis of a feed composition including at least one of lactic acid, glycerol, a five carbon sugar, a five carbon sugar alcohol, a six carbon sugar and a six carbon sugar alcohol to produce a bioderived propylene glycol product as well as guard against the leaching of metals such as nickel from the catalyst that has been observed to occur under acidic conditions in previous work, while greatly limiting the amounts of the four-carbon and higher diols that are formed and preferably substantially avoiding formation of any pentanediol byproducts altogether.

DESCRIPTION OF ILLUSTRATIVE
EMBODIMENTS OF THE INVENTION

The present invention may be beneficially employed in a number of processes such as have been mentioned for producing bioderived propylene glycol, in that the reaction pathways for the conversion of any of lactic acid, glycerol, five carbon sugars, five carbon sugar alcohols, six carbon sugars and six carbon sugar alcohols to propylene glycol and for the formation of the undesirable four carbon and higher diols are essentially common to all of these processes, though, as already established by Maris et al., the different catalysts used in these processes may respond somewhat differently to certain amounts of added base under the reaction conditions described as suited for these various catalysts.

In general, in all such processes in which added base or basic pH conditions can be realistically employed (Raney copper catalysts, for example, tend to undergo loss of the aluminum support under basic conditions) there will be an initially targeted level of added base for realizing or substantially realizing the highest conversion that can be achieved without producing four carbon and higher diols in the product mixture, and base will be added at one or more places along the length of a reactor in a continuous process or at one or more times after the beginning of a batch in a batchwise or semi-batch process to cause the initially targeted value to be approached downstream or after the initiation of a batch. Those skilled in the art will accordingly understand that specific embodiments described in greater detail hereafter are not to be considered limiting of the present invention as applied for the production of bioderived propylene glycol.

A preferred application of a process according to the present invention will be for improving the hydrogenolysis of glycerol to produce bioderived propylene glycol, particularly a process of a type described in Werpy '085 wherein glycerol is reacted with hydrogen in the presence of a rhenium-containing multimetallic catalyst to produce a bio-derived propylene glycol.

In a process of a type according to Werpy '085 employing a Ni/Re on carbon catalyst as exemplified therein, we have found that by using a targeted initial concentration of from 0.05 percent by weight to 0.3 percent by weight of NaOH (or the equivalent of another base), then adding an equivalent amount of NaOH in one or more places downstream in a continuous process or at one or more later points in time in a batch context, a greater overall conversion can be achieved of the glycerol and with a much reduced level of production of the four carbon and higher diols as compared to the circumstance wherein the same amount of NaOH in total is added at the beginning of the process.

In a preferred embodiment, the targeted initial concentration will be such that a minimal amount of the butanediols and substantially no pentanediol byproducts would be formed in a conventional single addition point mode of operation, and the number and placement or timing of further NaOH (or other base) additions will be such that again substantially no pentanediol byproducts are formed even as the overall conversion of glycerol is increased compared to the circumstance where there are no further base additions. In the context of a process using the same Ni/Re on carbon catalyst and operating on a 40% by weight glycerol/water feed at a liquid hourly space velocity of from 0.7 to 1.4 $hr^{-1}$, with a hydrogen pressure of between 10.3 to 13.8 MPa, gauge (1500 to 2000 pounds per square inch, gauge) and preferably from 11.7 to 12.4 MPa, gauge (1700 to 1800 psig of hydrogen) and at a temperature of between 200 and 220 degrees Celsius, a targeted initial concentration of NaOH at the start of the reactor or beginning of a batch would be from 0.1 to 0.2 percent by weight to substantially avoid formation of any pentanediol byproducts in a conventional single addition point mode of operation.

As demonstrated by the examples following, one or more subsequent additions of an equivalent amount of NaOH are effective for increasing the overall conversion in the process to an extent that would be consistent with a higher level of base addition in a single addition point mode of operation, but without producing the amounts of four carbon and higher diols that would be associated with that higher level of base addition in a single addition point mode of operation.

The present invention is further demonstrated by the non-limiting examples that follow:

COMPARATIVE EXAMPLE 1 AND EXAMPLES 1 AND 2

A 30 cubic centimeter fixed-bed stainless steel reactor having an internal diameter (ID) of 0.61 inches was loaded with a 5% Ni/1% Re on carbon catalyst, with stainless steel wool plugs at the top and bottom of the reactor. The reactor was jacketed and heated with a circulating oil. The reactor temperature was monitored by measuring the oil temperature, by means of an internal 1/8" thermowell with an external 1/16" slidable thermocouple to monitor peak temperature. The reactor temperature was controlled by adjustments in the oil temperature. An ISCO high pressure liquid metering pump was used to supply a mixed hydrogen/liquid feed to the reactor, with a mass flow controller being used to supply the hydrogen. The reactor outlet was attached to a condenser kept at 5 degrees Celsius by a chiller unit. The pressure within the reactor was controlled using a dome-loaded back pressure regulator.

Using this arrangement, hydrogen was supplied to the reactor at 1800 psig and at a flow rate of 1 liter/minute, together with a liquid feed comprised of 40 percent by weight glycerol feed in water and containing 0.1 percent by weight of added NaOH. The reaction temperature was maintained at 205 degrees Celsius. The liquid hourly space velocity for the liquid feed was set at 1.0 $hr^{-1}$.

Experiments were conducted with a single point addition of the 0.1 percent by weight of NaOH (Run 1), with recycling the entire product and adding a further 0.1 percent of NaOH (Run 2), and with recycling the entire product again and adding a further 0.1 percent of NaOH (Run 3).

The percentage of glycerol converted and the proportion of ethylene glycol, lactic acid, butanediols and pentanediol to the desired propylene glycol product were noted for all three runs along with the pH of the final product mixture at the conclusion of each run. Results were as shown in Table 1 below:

TABLE 1

|  | Run 1 | Run 2 | Run 3 |
|---|---|---|---|
| Glycerol conversion (%) | 30 | 60 | 85 |
| EG/PG (%) | 4.3 | 4.8 | 5.2 |
| Lactic acid/PG (%) | 2.8 | 2.5 | 2.3 |
| BDO/PG (ppm) | 0 | 0 | 790 |
| PDO/PG (ppm) | 0 | 0 | 0 |
| Product pH | 7.8 | 8.7 | 9.6 |

COMPARATIVE EXAMPLES 2 AND 3

To better illustrate the present invention's benefits, two additional experiments were done with the same apparatus and under the same conditions as used in Comparative Example 1 and Examples 1 and 2, with one experiment at 0.3 percent by weight of NaOH added to the reactants entering the reactor in a single addition point mode of operation, and the second at 1.0 percent by weight of NaOH added to the reactants entering the reactor. The results are shown in Table 2 as follows:

TABLE 2

|  | 0.3% NaOH | 1.0% NaOH |
|---|---|---|
| Glycerol Conversion (%) | 63 | 93 |
| EG/PG (%) | 5.6 | 7.5 |
| Lactic acid/PG (%) | 2.6 | 2.9 |
| BDO/PG (ppm) | 6388 | 15960 |
| PDO/PG (ppm) | nd | 4863 |
| Product pH | 11.6 | 12.6 |

What is claimed is:

1. In a process of making bioderived propylene glycol by reacting a feed composition including at least one of lactic acid, glycerol, a five carbon sugar, a five carbon sugar alcohol, a six carbon sugar and a six carbon sugar alcohol with hydrogen in the presence of a suitable catalyst for catalyzing the reaction and under conditions effective for carrying out the reaction, the improvement comprising:
   establishing a targeted pH value beyond which pentanediols begin to be formed;
   initiating the reaction of the feed composition and hydrogen in the presence of the catalyst at a pH value not exceeding the targeted pH value; and
   adding base as the reaction proceeds to adjust the pH in the reaction system toward the targeted pH value, but not exceeding the same.

2. An improved process according to claim 1, wherein the process is a continuous process and wherein base is added to a reactor in which the reaction is carried out, in at least one location downstream of the reactor inlet.

3. An improved process according to claim 2, wherein the amount of base added in each such downstream location is substantially the same as was added to the reactor at its inlet.

4. An improved process according to claim 1, wherein the process is conducted in a batchwise manner and wherein base is added to a reactor in which the reaction is carried out, at one or more times after the initiation of a batch.

5. An improved process according to claim 4, wherein the amount of base added at each such time is substantially the same as added at the initiation of a batch.

6. An improved process according to claim 2, wherein:
the feed composition comprises glycerol;
the catalyst comprises rhenium and nickel;
the amount of base added at the reactor inlet is from 0.05 to 0.3 percent by weight of the feed composition of sodium hydroxide or the equivalent amount of another base; and
the same amount of sodium hydroxide or the same equivalent amount of the same other base is added to the reactor after the initiation of the reaction.

7. An improved process according to claim 1, wherein the process is carried out at from 200 to 220 degrees Celsius, a liquid hourly space velocity of from 0.7 to 1.4 $hr^{-1}$ and a hydrogen pressure of from 10.3 MPa to 13.8 MPa, gauge.

8. An improved process according to claim 7, wherein the process is carried out at a hydrogen pressure of from 11.7 to 12.4 MPa, gauge.

9. A continuous process for making bioderived propylene glycol, comprising:
causing an aqueous feed composition comprising glycerol to react with hydrogen in the presence of a catalyst comprising rhenium and nickel and further with the addition at initiation of the reaction of from 0.05 to 0.2 weight percent of the aqueous feed composition of sodium hydroxide or an equivalent amount of another base; and
adding the same amount of sodium hydroxide or an equivalent amount of the same other base to the reactor in which the process is carried out, after the initiation of the reaction.

* * * * *